(12) United States Patent
Monty

(10) Patent No.: US 8,251,984 B2
(45) Date of Patent: Aug. 28, 2012

(54) DENTAL LASER SYSTEM USING MIDRANGE GAS PRESSURE

(75) Inventor: Nathan Monty, Charlton, MA (US)

(73) Assignee: Convergent Dental, Inc., Natick, MA (US)

( * ) Notice: Subject to any disclaimer, the term of this patent is extended or adjusted under 35 U.S.C. 154(b) by 229 days.

(21) Appl. No.: 12/847,739

(22) Filed: Jul. 30, 2010

(65) Prior Publication Data

US 2011/0027744 A1 Feb. 3, 2011

Related U.S. Application Data

(60) Provisional application No. 61/229,997, filed on Jul. 30, 2009.

(51) Int. Cl.
*A61B 18/18* (2006.01)

(52) U.S. Cl. .......... 606/10; 606/13; 606/11; 606/2; 607/89; 607/88

(58) Field of Classification Search .......... 606/10, 606/13, 11, 2; 607/89, 88
See application file for complete search history.

(56) References Cited

U.S. PATENT DOCUMENTS

| | | | |
|---|---|---|---|
| 4,874,315 A | 10/1989 | Featherstone et al. | |
| 5,310,471 A | 5/1994 | Markle et al. | |
| 5,342,198 A | 8/1994 | Vassiliadis et al. | |
| 5,401,171 A * | 3/1995 | Paghdiwala | 433/215 |
| 5,456,603 A * | 10/1995 | Kowalyk et al. | 433/215 |
| 5,748,663 A * | 5/1998 | Chenausky | 372/64 |
| 6,198,762 B1 * | 3/2001 | Krasnov | 372/87 |
| 6,339,913 B1 | 1/2002 | Leon Fong et al. | |
| 6,558,372 B1 | 5/2003 | Altshuler | |
| 6,558,374 B1 | 5/2003 | Brugger et al. | |
| 6,709,269 B1 | 3/2004 | Altshuler | |
| 2004/0024388 A1 | 2/2004 | Altshuler | |
| 2007/0189353 A1 | 8/2007 | Monty | |

OTHER PUBLICATIONS

International Search Report dated Apr. 20, 2011 issued in corresponding International Application No. PCT/US2010/043968.

Fan, Kenneth, et al. "A High Repetition Rate TEA CO2 Laser Operating at lambda=9.3-(mu)m for the Rapid and Conservative Ablation and Modification of Dental Hard Tissues," Lasers in Dentistry XII, Proc. of SPIE, vol. 6137, 2006, pp. 1-10.

Assa, Shlomo, et al. "Ablation of Dental Hard Tissues with a Microsecond Pulsed Carbon Dioxide Laser Operating at 9.3-(mu)m with an Integrated Scanner," Lasers in Dentistry XIV, Proc. of SPIE, vol. 6843, 2008, pp. 1-7.

\* cited by examiner

*Primary Examiner* — Kinam Park

(57) ABSTRACT

An improved dental laser system includes a DC power section that rectifies its AC electrical input energy in a format suitable for both CW and pulsed operation, an RF power supply operating in a range of about 40 to 125 MHz and configured for both CW and high peak power pulsing operation, a sealed-off, RF excited $CO_2$ waveguide or slab resonator laser filled to a gas at a pressure between about 260 to 600 Torr (or about 34,700-80,000 Pa), and a beam delivery system to steer the beam from the output of the laser to the mouth, such as the patient's mouth.

21 Claims, 2 Drawing Sheets

DENTAL LASER SYSTEM USING MIDRANGE GAS PRESSURE

CROSS REFERENCES TO RELATED APPLICATIONS

This application claims priority under 35 U.S.C. §119(e) to co-pending, commonly owned U.S. provisional patent application Ser. No. 61/229,997, entitled DENTAL LASER SYSTEM USING MIDRANGE GAS PRESSURE, filed Jul. 30, 2009, which is incorporated herein in its entirety by reference.

FIELD OF INTEREST

The present invention relates to systems and methods for removing decay, cutting, drilling or shaping hard tissue, removing and cutting soft tissue, modifying hard tissue for caries inhibition and modifying hard tissue surface conditions to aid in adhesion to hard tissue. The present invention applies to oral tissue, gums and teeth, e.g., to human or animal oral tissue, gums and teeth.

BACKGROUND

A tooth has three layers. The outermost layer is the enamel which is the hardest and forms a protective layer for the rest of the tooth. The middle and bulk of the tooth is made up of the dentin, and the innermost layer is the pulp. The enamel and dentin are similar in composition and are roughly 85% mineral, carbonated hydroxyapatite, while the pulp contains vessels and nerves which are sensitive to pressure and temperature. In this application of drilling or contouring or conditioning the enamel and dentin, the pulp's temperature sensitivity is of concern. A rise in temperature of 5.5° Celsius can lead to permanent damage of the tooth's pulp.

Over the last 10 to 15 years, research has taken place to define laser parameters that allow the enamel and dentin of a tooth to be removed, drilled, contoured or conditioned, all being removal processes, without heating the pulp. Ideally the laser pulses should vaporize the enamel and dentin converting the mass to gas with minimal residual energy remaining in the dentin to heat the pulp.

The use of lasers in dentistry has been considered since the introduction of the laser. Dental lasers used to drill and cut were the initial applications. High energy density pulses were initially used, but these pulses could potentially damage the tooth pulp or soft tissue, so lower energy pulse configurations were explored. With lower peak power energy pulses longer pulse times were used, which affected the tooth enamel detrimentally.

Various laser wavelength interactions were explored, UV to the Far Infrared, to understand the optical coupling efficiencies. Optical coupling was found to be critical with the greatest coupling being in the 2.7-3.0 μmeter and 9.3-9.6 μm wavelength ranges. When reflectance is considered, the 9.3-9.6 μmeter range was found to couple up to 3 times better than any other wavelength range.

Having identified the most effective coupling wavelength, the time and threshold to ablate hard tissue had to be determined. Research has shown that the thermal relaxation time of hard tissue is 1 to 2 μsec with a threshold ablation energy of approximately 5 mJ (milli-Joules).

Recognizing the need for laser pulses in the 9.3 to 9.6 μmeter wavelength range with microsecond pulse widths and pulse energies of 5 to 15 mJ, DC excited TEA (transversely excited atmospheric) lasers were adopted. Since the TEA lasers have a very short pulse length, i.e., hundreds of nanoseconds, the TEA lasers were modified for long pulse operation and modified pulse shapes. Additionally a RF (Radio Frequency) CW (continuous wave) laser was studied, but its shortest pulse length was only 50 μseconds, so the pulses heated the hard tissue significantly more than the shorter pulse widths.

To date, RF excited $CO_2$ CW lasers seeking the greatest RF to Optical efficiency typically operate at 70 to 100 Torr (or about 9,332-13,332 Pascals (Pa)) and the shortest pulse lengths produced are typically 50 μseconds. Typical gas pressure for a normal RF excited $CO_2$ laser, used in the prior art, is 80 Torr (or about 10,665 Pa). $CO_2$ TEA lasers operating at atmospheric pressure produce 9.3 to 9.6 μmeter pulses at hundreds of nanoseconds in pulse length. TEA lasers generally do not operate in sealed operation, do not have long operating lifetimes or high pulse repetition rates, and are expensive to package. While a "long pulse" TEA laser can be manufactured to produce the optimal $CO_2$ laser pulsing parameters, TEA lasers are larger and more expensive than RF excited lasers and therefore are not an ideal match for a dental laser application—where size and cost are critical. None of the approaches to date, therefore, have produced a full set of optimal parameters in a commercially acceptable format for effectively working with enamel and dentin, without heating the pulp.

SUMMARY

In accordance with one aspect of the present disclosure, provided is a $CO_2$ dental laser system comprising a direct current (DC) power supply, a radio frequency (RF) power supply coupled to the DC power supply, a $CO_2$ laser filled with gas at a pressure in a range of about 260 to 600 Torr (or about 34,700-80,000 Pa), and a beam delivery system configured to steer laser optical energy output from the laser to a patient.

In some embodiments, the pressure can be in a range of about 280-550 Torr (or about 37,330-73,327 Pa), about 300-500 Torr (or about 39,996-66,661 Pa), about 320-450 Torr (or about 42,663-59,995 Pa), about 340-400 Torr (or about 45,329-53,328 Pa), as examples.

In any of the preceding embodiments, the laser can include a hybrid unstable-waveguide resonator commonly referred to as a slab resonator.

In any of the preceding embodiments, the laser can include a waveguide resonator.

In any of the preceding embodiments, the laser can be filled with $^{12}C(^{18}O)_2$ gas.

In any of the preceding embodiments, the laser can be filled with $^{12}C(^{16}O)_2$ gas.

In any of the preceding embodiments, the laser resonator mirrors can be coated to preferentially resonate within a wavelength range of about 9.3 to 9.6 μmeters.

In any of the preceding embodiments, the DC power supply can include a low power continuous power section coupled to a capacitor bank to support high peak power pulsing.

In any of the preceding embodiments, the RF power supply can be operated with a range of about 40 to 125 Mhz.

In any of the preceding embodiments, the RF power supply can include a set of high peak power pulsing RF transistors that operate in a range from continuous wave (CW) to about 25 KHz, with a duty cycle in a range of about 0 to 60%.

In any of the preceding embodiments, the beam delivery system can include a combination of flat or curved mirrors that steer the optical output energy from the $CO_2$ laser.

In any of the preceding embodiments, the beam delivery system can be a hollow waveguide.

In any of the preceding embodiments, the $CO_2$ laser can be operated in a pulsed mode and output the gas in pulses having a rise and fall time of not more that about 50 μsecond.

In accordance with another aspect of the present invention, provided is a $CO_2$ dental laser system comprising: a direct current (DC) power supply, a radio frequency (RF) power supply coupled to the DC power supply, a $CO_2$ laser filled with gas at a pressure in a range of about 260 to 600 Torr (or about 34,700-80,000 Pa), and a beam delivery system configured to steer laser optical energy output from the $CO_2$ laser to a patient. The DC power supply is comprised of a continuous wave (CW) DC section and a pulsed DC section.

In some embodiments, the pressure can be in a range of about 280-550 Torr (or about 37,330-73,327 Pa), about 300-500 Torr (or about 39,996-66,661 Pa), about 320-450 Torr (or about 42,663-59,995 Pa), about 340-400 Torr (or about 45,329-53,328 Pa), as examples.

In any of the preceding embodiments, the DC section can be configured to run the $CO_2$ laser for CW applications and the pulsed DC section can be configured to run the $CO_2$ laser at peak energy for pulsing applications.

In any of the preceding embodiments, the $CO_2$ laser can include a slab resonator.

In any of the preceding embodiments, the $CO_2$ laser can include a waveguide resonator.

In any of the preceding embodiments, the gas can be a $^{12}C(^{18}O)_2$ gas.

In any of the preceding embodiments, the gas can be a $^{12}C(^{16}O)_2$ gas.

In any of the preceding embodiments, the $CO_2$ laser can be operated in a pulsed mode and output optical energy having a wavelength of 9.3 to 9.6 μmeter, and a rise and fall time of not more that about 50 μseconds.

In accordance with another aspect of the invention, provided is a $CO_2$ dental laser system comprising: a direct current (DC) power supply; a radio frequency (RF) power supply coupled to the DC power supply; a $CO_2$ laser filled with gas at a pressure in a range of about 260 to 600 Torr (or about 34,700-80,000 Pa); and a beam delivery system configured to steer laser optical energy output from the from the $CO_2$ laser to a patient. The $CO_2$ laser is operated in a pulsed mode and outputs optical energy having a wavelength of 9.3 to 9.6 μmeter, and a rise and fall time of not more that about 50 μseconds.

In some embodiments, the pressure can be in a range of about 280-550 Torr (or about 37,330-73,327 Pa), about 300-500 Torr (or about 39,996-66,661 Pa), about 320-450 Torr (or about 42,663-59,995 Pa), about 340-400 Torr (or about 45,329-53,328 Pa), as examples.

In accordance with yet another aspect of the invention, provided is a method of outputting laser optical energy from a $CO_2$ dental laser system. The method includes providing a direct current (DC) power supply, providing a radio frequency (RF) power supply coupled to the DC power supply, filling a $CO_2$ laser with gas at a pressure in a predetermined pressure range (e.g., of about 260 to 600 Torr (or about 34,700-80,000 Pa)), and steering the laser optical energy output from the from the $CO_2$ laser to a patient using a beam delivery system.

In some embodiments, the pressure can be in a range of about 280-550 Torr (or about 37,330-73,327 Pa), about 300-500 Torr (or about 39,996-66,661 Pa), about 320-450 Torr (or about 42,663-59,995 Pa), about 340-400 Torr (or about 45,329-53,328 Pa), as examples.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings.

DETAILED DESCRIPTION OF PREFERRED EMBODIMENTS

Figure 1:
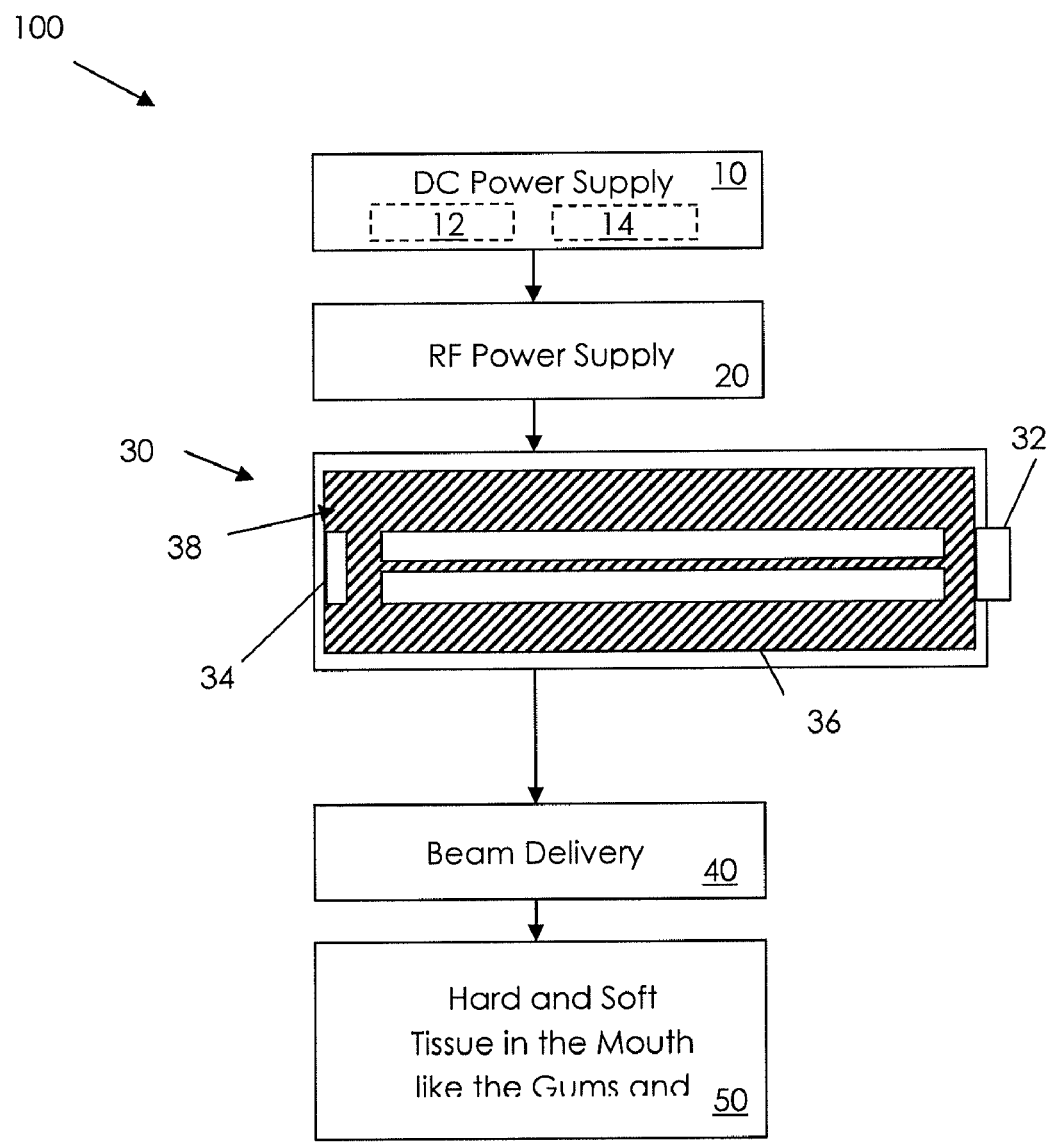
FIG. 1 is a block diagram of an embodiment of a dental laser system, in accordance with aspects of the present invention.

Hereinafter, aspects of the present invention will be described by explaining illustrative embodiments in accordance therewith, with reference to the attached drawings. While describing these embodiments, detailed descriptions of well-known items, functions, or configurations are typically omitted for conciseness.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

With respect to dental laser systems, the wavelength with the highest absorption in hydroxyapatite has been determined to be in the 9.3 to 9.6 μmeter range and the thermal relaxation time of hydroxyapatite to be a maximum of 2 μseconds at 9.3 to 9.6 μm wavelength range. Therefore, the ideal pulse parameters for removing the hydroxyapatite appear to be 9.3 to 9.6 μmeter energy in a less than 50 μsecond format. In accordance with the preferred embodiment, a laser is provided that produces a beam having pulse parameters for removing hydroxyapatite using 9.3 to 9.6 μm wavelength energy in a less than 50 μsecond format.

The 9.3 to 9.6 μm energy is typically produced using a $CO_2$ laser with a laser gas mixture of $^{12}C(^{18}O)_2$, wavelength selective resonator optics, more expensive inter-cavity wavelength devices, or a combination of the three. In accordance with the present invention, the 50 μsecond pulses are produced with a fast pulse rise and fall time, which is effected by laser gas pressure. In order to produce pulses of less than or equal to 50 µseconds in length, with gas pressure of at least about 260 Torr (or about 34,663 Pa).

According to preferred embodiment, a $CO_2$ gas laser, in either a waveguide or slab resonator format, filled with gas that is in a range of about 260 Torr to 600 Torr (or about 34,700-80,000 Pa), which is RF excited for use in all dental applications. A range of about 260 to 600 Torr (or about 34,700-80,000 Pa) may be preferable in many dental applications. Since waveguide and slab resonators are generally known in the art, they are not discussed in detail herein.

In some embodiments, the pressure can be in a range of about 280-550 Torr (or about 37,330-73,327 Pa), about 300-500 Torr (or about 39,996-66,661 Pa), about 320-450 Torr (or about 42,663-59,995 Pa), about 340-400 Torr (or about 45,329-53,328 Pa), as examples.

The laser can be operated in CW or pulsed mode for cutting and drilling applications, respectively. DC and RF power supplies are configured to aid in low power CW operation, while supporting high peak power pulse operation. The laser output is coupled to a beam delivery system to deliver the optical energy to the patient. The laser provides the 9.3 to 9.6 µm energy wavelength, with a fast pulse rise and fall time (e.g., not more than about 50 µseconds, and preferably not more than 20 µsecond), sealed off operation, high repetition rates in a small reliable package.

FIG. 1 shows an embodiment of a dental laser system 100 according to aspects of the present invention. In the embodiment of FIG. 1, a DC power supply 10 is provided that rectifies as AC input power (not shown). In the preferred embodiment, the DC power supply 10 is comprised of a continuous wave (CW) DC section 12 and a pulsed DC section 14. The DC section 12 is sized to run the laser for CW applications, such as soft tissue cutting, and the peak power DC section 14 supplies the peak energy for pulsing applications, such as hard tissue modification.

Item 20 is a radio frequency (RF) power supply for the conversion of the DC energy to RF energy in the 40 to 125 MHZ range. Item 30 is a $CO_2$ laser with the RF energy as an input and 9.3 to 9.6 µmeter optical energy as an output, via an output coupler 32. And item 40 is a beam delivery apparatus, which delivers the optical energy from the laser to item 50, which represents a patient's mouth.

$CO_2$ laser 30 in this embodiment includes a rear mirror 34 and a laser discharge area 36. The mirror 34 directs optical energy through the laser discharge area 36. The output coupler 32 couples the beam out of the laser. In this case the laser is a gas laser, so the output coupler couples the beam out of the laser without allowing the laser gas out. The $CO_2$ laser 30 also includes a laser gas pressure vessel 38 that is filled with a gas at a pressure in a range of about 260 to about 600 Torr (or about 34,700-80,000 Pa).

The output laser energy is provided to the beam delivery apparatus 40, where it can then be directed to a target, such as a patient's mouth. In this embodiment, the beam delivery apparatus 40 can include a combination of flat or curved mirrors configured to steer optical energy output from the $CO_2$ laser.

In this exemplary configuration, the dental laser system 100 can operate at both low power CW operation, e.g., <10 watts, for the cutting of gums and oral tissue, and high peak power pulsing operation, e.g., >5 mJ pulse energy at 1 to 50 µseconds pulse widths up to 10 KHz. The $CO_2$ laser 30 can operate at wavelengths between 9 and 11 µm. The laser system 100 preferably provides high peak power pulsing operation at the ideal absorption wavelength for the hydroxyapatite in dental hard tissues. The pulse widths and pulse energy are ideally suited to ablate hydroxyapatite, leaving very little residual heat in the tooth to damage the pulp even up to 10 KHz in operation.

Figure 2:
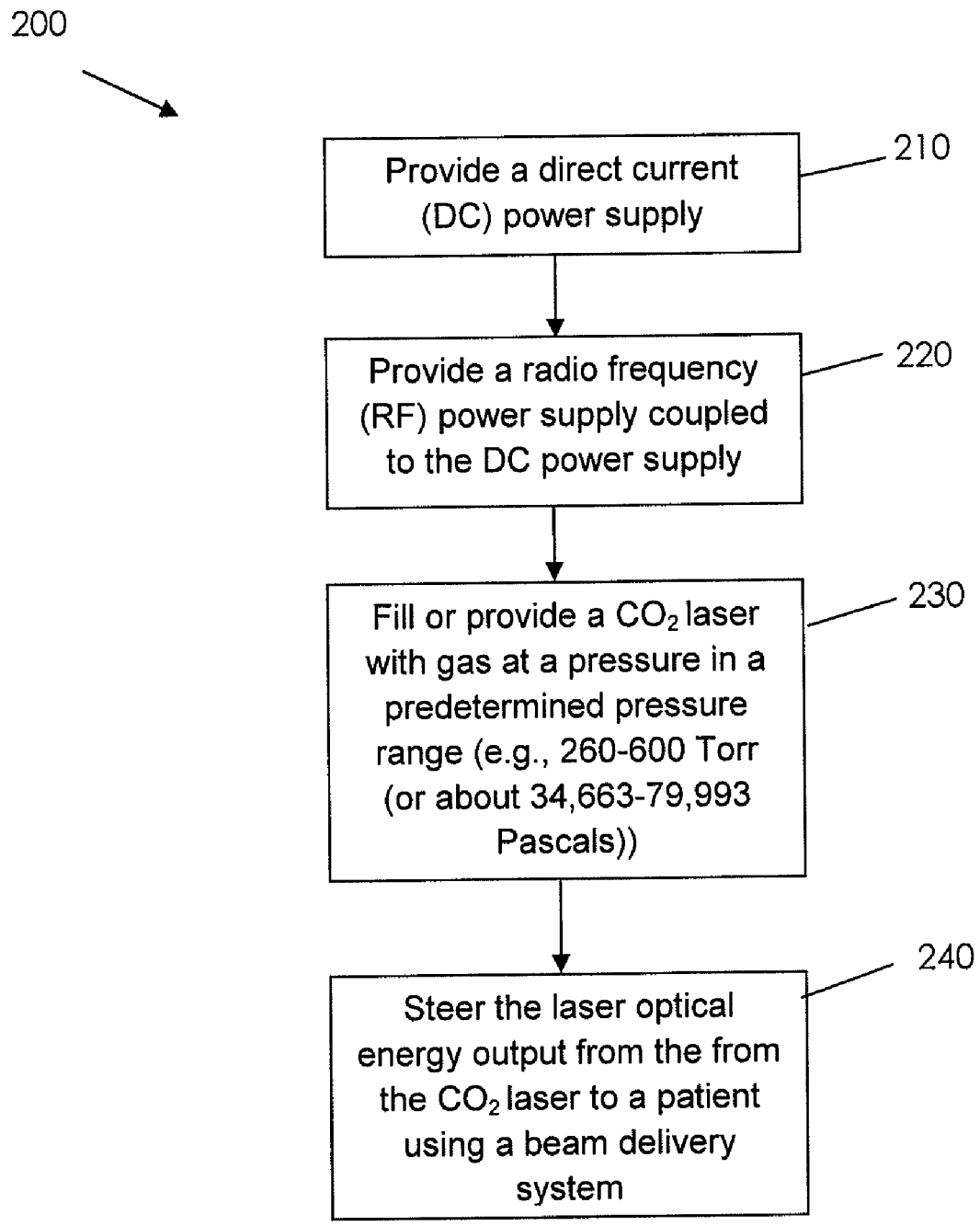
FIG. 2 is a flowchart of an embodiment of outputting laser optical energy from a $CO_2$ dental laser system, in accordance with aspects of the present invention.

FIG. 2 is an embodiment of a method of outputting laser optical energy from a $CO_2$ dental laser system. The method 200 includes providing a direct current (DC) power supply in step 210, providing a radio frequency (RF) power supply coupled to the DC power supply in step 220, filling a $CO_2$ laser with gas at a pressure in a predetermined pressure range (e.g., about 260 to 600 Torr (or about 34,700-80,000 Pa)) in step 230, and steering the laser optical energy output from the from the $CO_2$ laser to a patient using a beam delivery system 240.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. For example, it is possible that the described laser and laser system could be used in other (non-dental) applications. It is intended by the following claims to claim that which is literally described and all equivalents thereto, including all modifications and variations that fall within the scope of each claim.

What is claimed is:

1. A $CO_2$ dental laser system comprising:
   a direct current (DC) power supply;
   a radio frequency (RF) power supply coupled to the DC power supply;
   a $CO_2$ laser filled with a gas at a pressure in a range of about 260 to 600 Torr; and
   a beam delivery system configured to steer laser optical energy output from the from the $CO_2$ laser to a patient.

2. The system of claim 1, wherein the $CO_2$ laser includes a slab resonator.

3. The system of claim 1, wherein the $CO_2$ laser includes a waveguide resonator.

4. The system of claim 1, wherein the gas is a $^{12}C(^{18}O)_2$ gas.

5. The system of claim 1, wherein the gas is a $^{12}C(^{16}O)_2$ gas.

6. The system of claim 1, wherein the laser includes a set of resonator mirrors coated to resonate within a wavelength range of about 9.3 to 9.6 µmeters.

7. The system of claim 1, wherein the DC power supply includes a low power continuous power section coupled to a capacitor bank to support high peak power pulsing.

8. The system of claim 1, wherein the RF power supply is configured to be operated within a range of about 40 to 125 Mhz.

9. The system of claim 1, wherein the RF power supply includes a set of high peak power pulsing RF transistors that operate in a range from continuous wave (CW) to about 25 KHz, with a duty cycle in a range of about 0 to 60%.

10. The system of claim 1, wherein the beam delivery system includes a combination of flat or curved mirrors configured to steer optical energy output from the $CO_2$ laser.

11. The system of claim 1, wherein the beam delivery system includes a hollow waveguide.

12. The system of claim 1, wherein the $CO_2$ laser is operated in a pulsed mode and outputs optical energy having a wavelength of 9.3 to 9.6 µmeter, and a rise and fall time of not more than about 50 µseconds.

13. A $CO_2$ dental laser system comprising:
    a direct current (DC) power supply, wherein the DC power supply is comprised of a continuous wave (CW) DC section and a pulsed DC section; a radio frequency (RF) power supply coupled to the DC power supply; a CO2 laser filled with a gas at a pressure in a range of about 260 to 600 Torr; and a beam delivery system configured to steer laser optical energy output from the from the $CO_2$ laser to a patient.

14. The system of claim 13, wherein the continuous wave (CW) DC section is configured to run the $CO_2$ laser for CW applications and the pulsed DC section is configured to run the $CO_2$ laser at peak energy for pulsing applications.

15. The system of claim 13, wherein the $CO_2$ laser includes a slab resonator.

16. The system of claim 13, wherein the $CO_2$ laser includes a waveguide resonator.

17. The system of claim 13, wherein the gas is a $^{12}C(^{18}O)_2$ gas.

18. The system of claim 13, wherein the gas is a $^{12}C(^{16}O)_2$ gas.

19. The system of claim 13, wherein the $CO_2$ laser is operated in a pulsed mode and outputs optical energy having a wavelength of 9.3 to 9.6 μmeter and a rise and fall time of not more than about 2 μseconds.

20. A $CO_2$ dental laser system comprising:
a direct current (DC) power supply;
a radio frequency (RF) power supply coupled to the DC power supply;
a $CO_2$ laser filled with a gas at a pressure in a range of about 260 to 600 Torr; and
a beam delivery system configured to steer laser optical energy output from the from the $CO_2$ laser to a patient, wherein the $CO_2$ laser is operated in a pulsed mode and outputs optical energy having a wavelength of 9.3 to 9.6 μmeter and a rise and fall time of not more than about 2 μseconds.

21. A method of outputting laser optical energy from a $CO_2$ dental laser system, the method comprising:
providing a direct current (DC) power supply;
providing a radio frequency (RF) power supply coupled to the DC power supply;
filling a $CO_2$ laser filled with a gas at a pressure in a range of about 260 to 600 Torr; and
steering the laser optical energy output from the from the $CO_2$ laser to a patient using a beam delivery system.

* * * * *